(12) United States Patent
Lee

(10) Patent No.: US 6,981,984 B2
(45) Date of Patent: Jan. 3, 2006

(54) STENT WITH COMBINED DISTAL PROTECTION DEVICE

(76) Inventor: Don W. Lee, 1510 S. Central, Suite 150, Glendale, CA (US) 91204

( * ) Notice: Subject to any disclaimer, the term of this patent is extended or adjusted under 35 U.S.C. 154(b) by 313 days.

(21) Appl. No.: 10/246,257

(22) Filed: Sep. 17, 2002

(65) Prior Publication Data

US 2004/0054394 A1    Mar. 18, 2004

(51) Int. Cl.
*A61F 2/06* (2006.01)
(52) U.S. Cl. .................................................. 623/1.11
(58) Field of Classification Search ............... 623/1.11; 606/108, 194, 195; 604/103.04–103.05, 604/99.02–99.03, 101.02–101.05, 102.02, 604/102.03
See application file for complete search history.

(56) References Cited

U.S. PATENT DOCUMENTS

| | | | |
|---|---|---|---|
| 5,639,274 A | | 6/1997 | Fischell et al. |
| 5,857,464 A | * | 1/1999 | Desai .......................... 600/435 |
| 6,346,116 B1 | | 2/2002 | Brooks et al. |
| 6,364,900 B1 | * | 4/2002 | Heuser ....................... 623/1.11 |
| 6,371,969 B1 | | 4/2002 | Tsugita et al. |

OTHER PUBLICATIONS

MEDTRONIC News Released dated Sep. 20, 2002 Results of Landmark SAFER Study Published in Circulation.
TRIACTIV Balloon Protected Flush Extraction System dated Aug. 20, 2002.
PercuSurge Because, even Small Particles can Cause Big Problems.

* cited by examiner

*Primary Examiner*—Tan-Uyen T. Ho
(74) *Attorney, Agent, or Firm*—James E. Brunton, Esq.

(57) ABSTRACT

A method and apparatus for introducing a stent into a region of a major blood vessel within the human body in a manner which substantially reduces the risk of embolic material escaping to the vessel and causing a blockage at a downstream location. A uniquely designed stent delivery catheter includes a central lumen through which a guide wire travels. The central lumen is provided with a valve means that is operable by the guide wire and when moved into a closed position by withdrawal of the guide wire, functions to prevent the flow of loose debris toward the proximal end of the catheter.

15 Claims, 7 Drawing Sheets

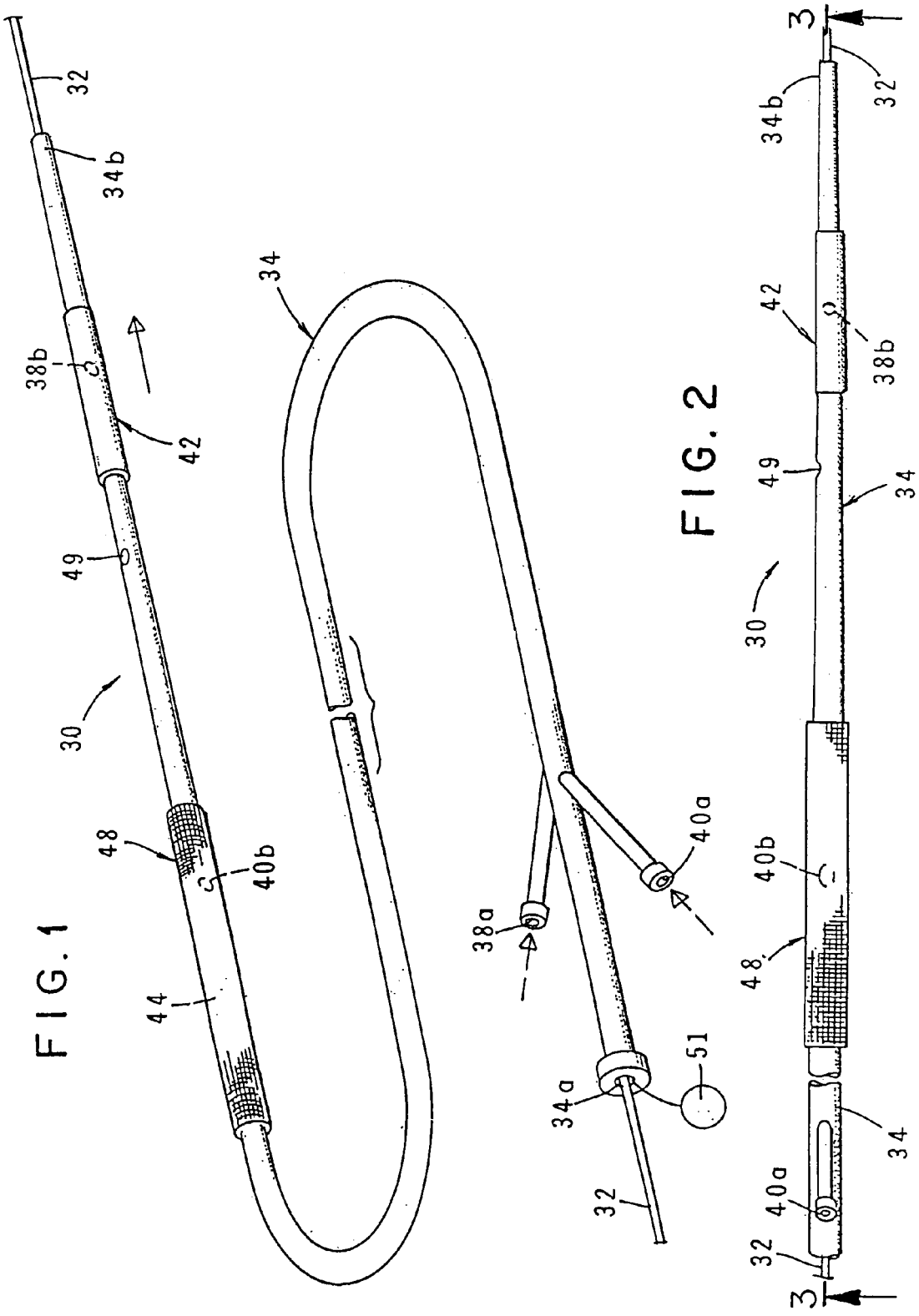

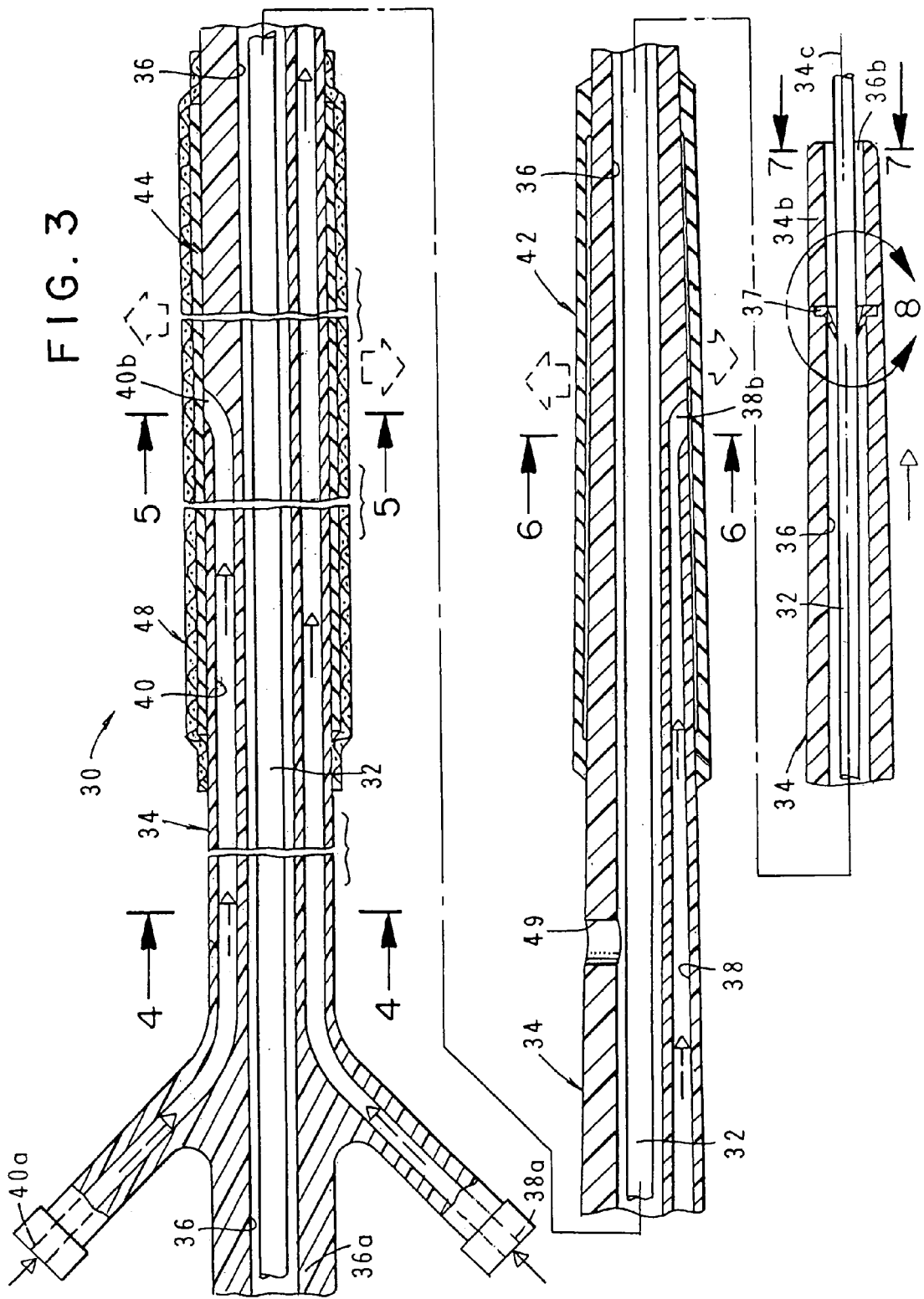

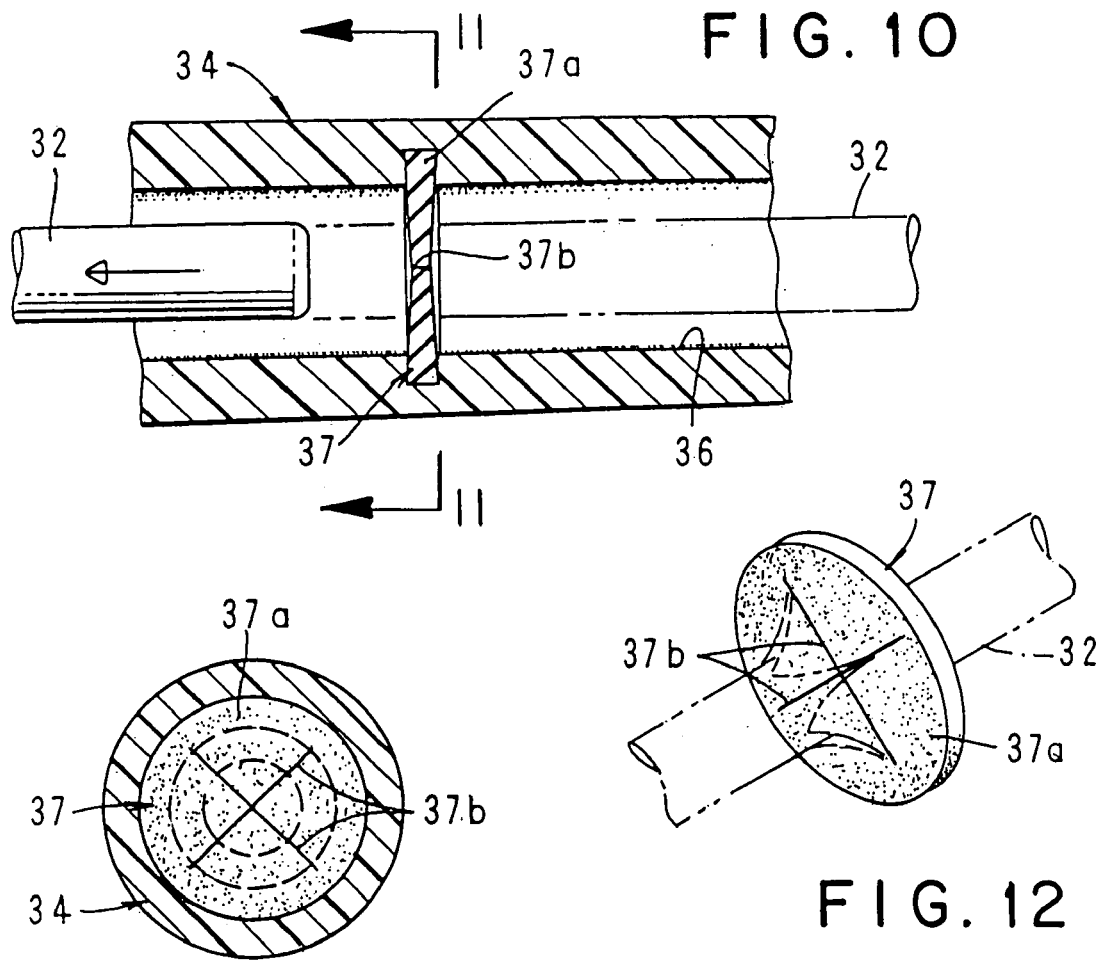
FIG. 10
FIG. 11
FIG. 12
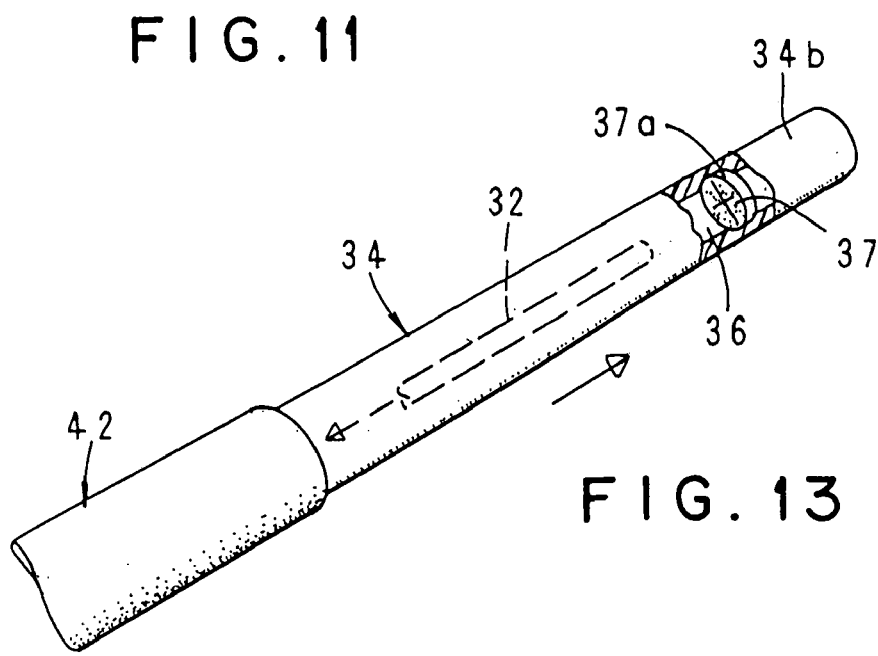
FIG. 13

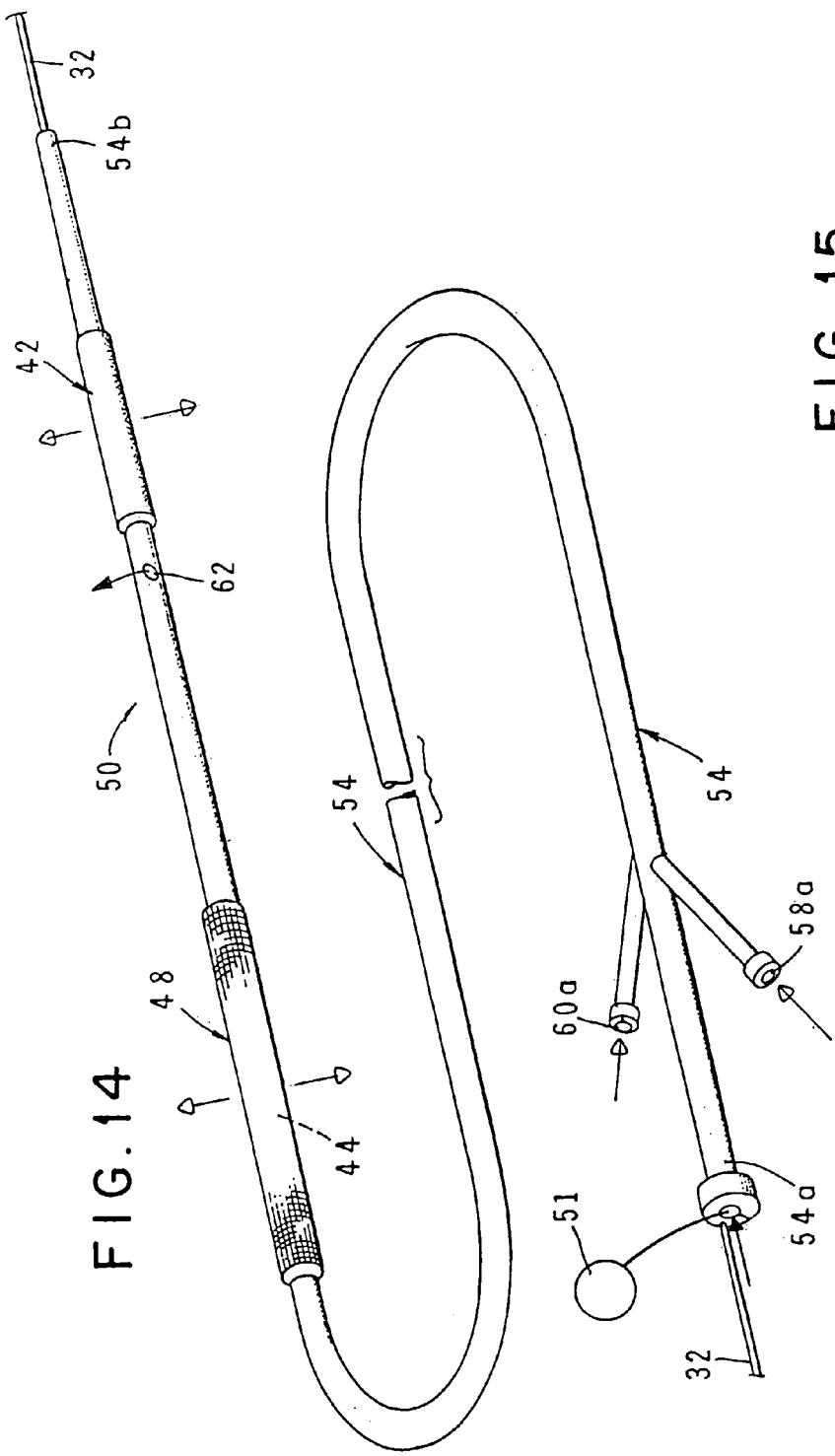

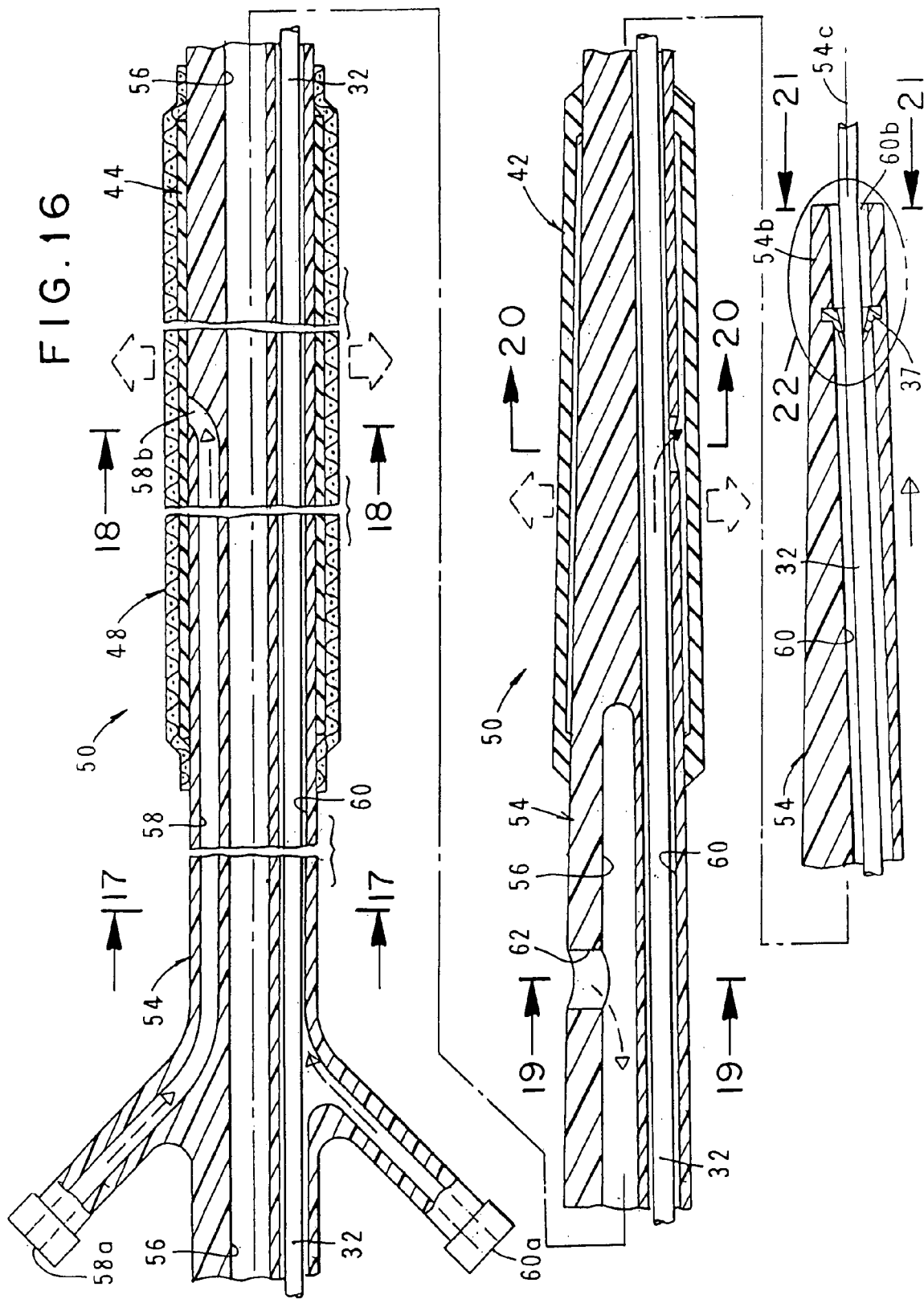

STENT WITH COMBINED DISTAL PROTECTION DEVICE

BACKGROUND OF THE INVENTION

1. Field of the Invention

The present invention relates generally to methods and apparatus for introducing a stent to into a region of a major blood vessel within the patient, such as the carotid artery, the renal artery and the coronary artery.

2. Discussion of the Prior Art

A number of procedures have been suggested in the past for opening stenosed or occluded blood vessels in a patient caused by the deposit of plaque or other material on the walls of the blood vessels. For example, angioplasty, is a well known procedure wherein an inflatable balloon is first introduced into the occluded region and then inflated, dilating the stenosed blood vessel in the manner to increase the intraluminal diameter.

Another well-known prior art procedure involves permanently or temporarily introducing a stent into the stenosed region to open the lumen of the vessel. The stent, which is readily commercially available from various sources, typically comprises a generally cylindrically shaped mesh sleeve made from such materials as stainless steel or nitinol. The unique design of the stent permits it to be radially expanded, while still providing sufficient rigidity to maintain its shape once it has been expanded to a desired size.

In the practice of the prior art stent emplacement procedures, the stent is introduced into the desired blood vessel using known percutaneous methods. More particularly, a catheter, having the stent affixed thereto, is directed to the region of the blood vessel being treated and is strategically positioned so that the stent is centered across the stenosed region. This done, the balloon is inflated, by introducing gas or fluid, through a lumen in the catheter communicating with the balloon. The controlled inflation of the balloon causes the stent to expand radially outward into engagement with the stenosed material. As the stent expands, the material is forced outward, dilating the lumen of the blood vessel. Once in position, the stent retains its expanded shape, providing an open passage for blood flow. The balloon is then deflated and the catheter withdrawn from the vessel.

During the stent emplacement procedure, plaque that has been deposited on the walls of the vessel may be set free and when this material travels downstream, it can cause serious complications. By way of example, loose embolic material released within the carotid arteries may travel downstream to the brain, possibly causing stroke, which can lead to permanent injuries and sometimes the death of the patient.

Thus, there is a need for an apparatus and method for delivering a stent into an arterial occlusion, which effectively prevents loose embolic material from traveling downstream and also prevents blood and embolic material from flowing through the guide wire lumen of the stent delivery catheter a direction toward the proximal end of the catheter.

In typical prior art balloon angioplasty procedures, a guiding catheter having a preformed distal tip is percutaneously introduced through the femoral artery into the cardiovascular system of a patient in accordance with conventional techniques. The guiding catheter is then advanced within the cardiovascular system until the distal tip is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon proximate the distal end thereof is advanced into the patient's coronary anatomy over the previously introduced guidewire until the balloon of the dilatation catheter is properly positioned across the lesion. Once in position across the lesion, the balloon is inflated to a predetermined pressure to compress the arteriosclerotic plaque of the lesion against the inside of the artery wall and to otherwise expand the inner lumen of the artery. The balloon is then deflated so that blood flow can be resumed through the dilated artery and the dilatation catheter can be removed.

Applicant is familiar with a prior art distal protection system that is available from Medtronic, Inc of Minneapolis, Minn. that is sold under the name and style "GUARDWIRE PLUS". This system, which contains the balloon at its the distal tip, is deployed across the lesion and is then inflated to occlude the vessel and prevent migration of embolic particles that may become dislodged during an intervention. The angioplasty balloon and stent systems are then advanced to the treatment side, where the dislodged large particles remain suspended in the occluded vessel. Upon completion of the interventional procedure, another catheter is introduced and the particles are aspirated. This done, the balloon is deflated and removed.

Applicant is also familiar with a prior art, balloon protected flush extraction system offered by the Kensey Nash Corp. of Exton, Pa. under the name and style "TRIACTIV". This system uses three distinct components, namely a guide wire with the distal protection balloon, a flexible 3 French flush catheter and active peristaltic pump flush and extraction systems. These three features work in concert to provide distal protection with debris extraction. Following stenting the protected space is flushed and any remaining loose debris is extracted.

Another prior art distal protection device is offered for sale by the Traatek Company of Miami, Fla. under the name and style "PERCUSURGE". This device is a balloon the occlusion thrombectomy device approved by the United States Food and Drug Administration for vein graft intervention.

SUMMARY OF THE INVENTION

It is an object of the present invention to provide a novel method and apparatus for introducing a stent into a region of a major blood vessel within the human body in a manner which substantially reduces the risk of embolic material escaping to the vessel and causing a blockage at a downstream location. More particularly it is an object of the invention to provide an apparatus and method to substantially contain loose embolic material within the aorta and the carotid arteries during an interventional procedure and thereby prevent it from reaching the brain.

Another object of the invention is to provide an apparatus of the aforementioned character which includes a uniquely designed stent delivery catheter having a central lumen through which a guide wire travels, the central lumen being provided with a valve means that is operable by the guide wire and when moved into a closed position by withdrawal of the guide wire functions to prevent bloodflow toward the proximal end of the catheter.

Another object of the invention is to provide a stent delivery system which includes a stent delivery catheter of a simple construction having mounted proximate the distal end thereof an angioplasty balloon of conventional design.

A stent expanding balloon, which carries a readily commercially available type of expandable stent is mounted intermediate of the distal and proximal ends of the catheter.

Another object of the invention is to provide an apparatus of the character described in the preceding paragraph, which includes a first side lumen for use in inflating the angioplasty balloon and a spaced apart second side lumen for use in inflating the stent expanding balloon.

Another object of the invention is to provide an apparatus as described in the preceding paragraph in which the cannula is provided with a third lumen that is in communication with the blood vessel via an opening in the cannula wall to permit the aspiration of embolic material residing within the blood vessel.

By way of summary, the present invention provides a method and apparatus for preventing embolic material from escaping a site of intervention within the carotid artery, the renal artery and like arteries. More specifically, the present invention provides an apparatus and method for introducing a stent into a region of a major blood vessel within the human body exhibiting plaque deposits, thereby opening the occlusion. The method and apparatus of the invention also prevents embolic material from traveling downstream within the blood vessel. Additionally, the apparatus of the invention includes a catheter of novel design that includes a central lumen provided with a uniquely designed check valve that, when moved into a closed position by withdrawal of the guide wire from the catheter lumen, substantially blocks the flow of blood and loose debris through the central lumen of the catheter in a direction toward the proximal end of the catheter.

BRIEF DESCRIPTION OF THE DRAWINGS

FIG. 1 is a generally perspective view of one form of the stent delivery system of the present invention.

FIG. 2 is a foreshortened, top view of the stent delivery system shown in FIG. 1.

FIG. 3 is a greatly enlarged, cross-sectional view taken along lines 3—3 of FIG. 2.

FIG. 10 is a cross-sectional view similar to FIG. 8, but showing the guide wire withdrawn and the check valve moved into a closed configuration.

FIG. 11 is a cross-sectional view taken along lines 11—11 of FIG. 10.

FIG. 12 is a fragmentary, generally perspective view of the valve means of the form of the invention shown in FIG. 1.

FIG. 13 is a fragmentary, generally diagrammatic, perspective view illustrating the placement of the catheter of the system over the guide wire.

FIG. 14 is a generally perspective view of an alternate form of the stent delivery system of the present invention.

FIG. 15 is a foreshortened, top view of the stent delivery system shown in FIG. 14.

FIG. 16 is a greatly enlarged cross-sectional view taken along lines 16—16 of FIG. 15.

DESCRIPTION OF THE INVENTION

Figure 4:
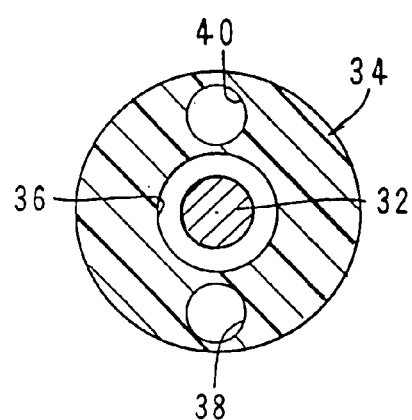
FIG. 4 is an enlarged cross sectional view taken along lines 4—4 of FIG. 3.

Referring to the drawings and particularly to FIGS. 1, 2 and 3, one form of the catheter system of the invention for balloon angioplasty and stent delivery is there illustrated and generally designated by the numeral 30. This system here comprises a guide wire 32 and an elongated catheter 34 having a proximal end 34a, a distal end 34b and an axial center line 34c. Catheter 34 is preferably formed of a biocompatible and hydrophilic compatible material, such as a lubricous polyimide or polyethylene. Other suitable materials for the catheter include nylons, urethanes, and polypropylene that are preferably compatible with coatings such as silicone and various hydrophilic coatings.

Figure 5:
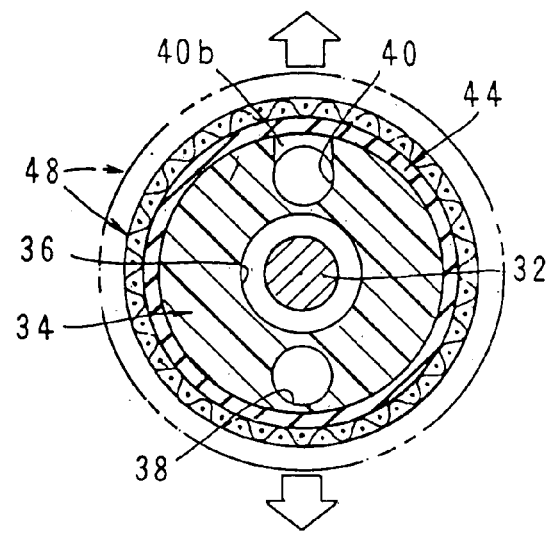
FIG. 5 is an enlarged cross sectional view taken along lines 5—5 of FIG. 3.
Figure 6:
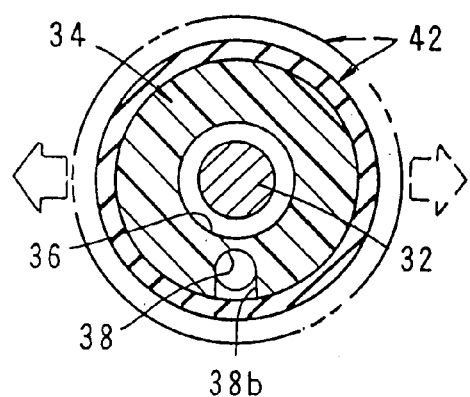
FIG. 6 is an enlarged cross sectional view taken along lines 6—6 of FIG. 3.
Figure 7:
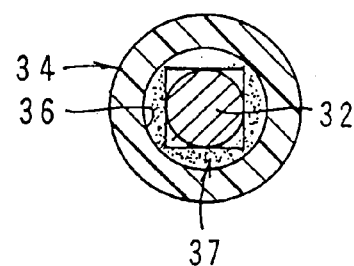
FIG. 7 is an enlarged cross sectional view taken along lines 7—7 of FIG. 3.
Figure 8:
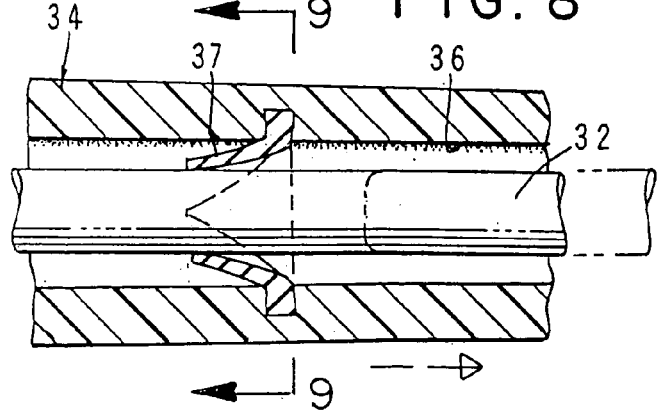
FIG. 8 is a greatly enlarged cross sectional view of the area designated in FIG. 3 by the numeral 8.
Figure 9:
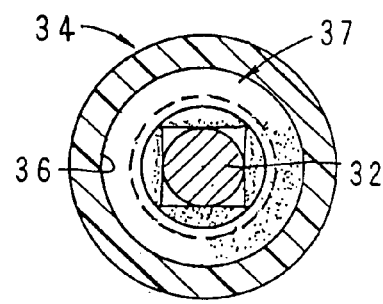
FIG. 9 is a cross-sectional view taken along lines 9—9 of FIG. 8.
Figure 17:
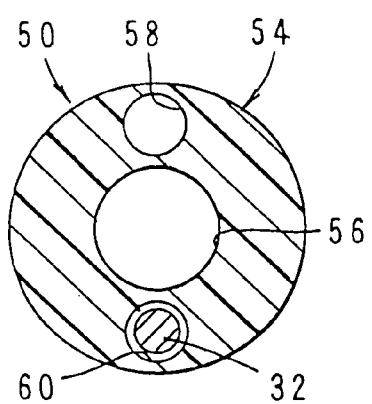
FIG. 17 is an enlarged cross sectional view taken along lines 17—17 of FIG. 16.
Figure 18:
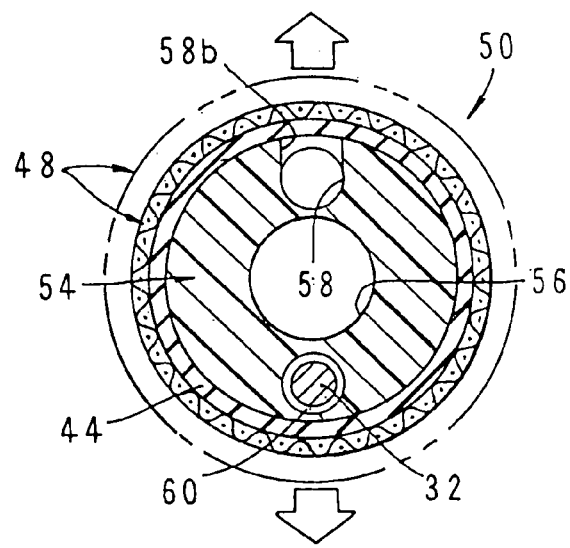
FIG. 18 is an enlarged cross sectional view taken along lines 18—18 of FIG. 16.
Figure 19:
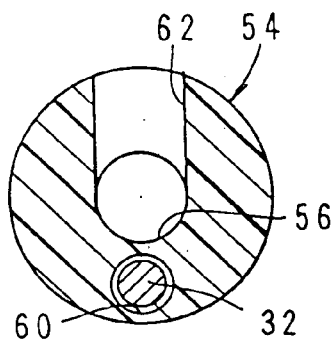
FIG. 19 is an enlarged cross sectional view taken along lines 19—19 of FIG. 16.
Figure 20:
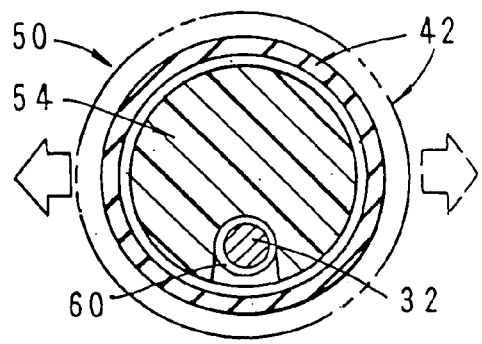
FIG. 20 is an enlarged cross sectional view taken along lines 20—20 of FIG. 16.
Figure 21:
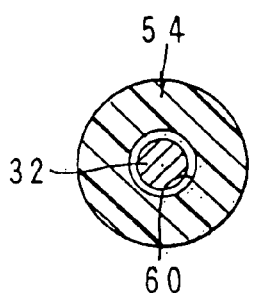
FIG. 21 is an enlarged cross sectional view taken along lines 21—21 of FIG. 16.
Figure 22:
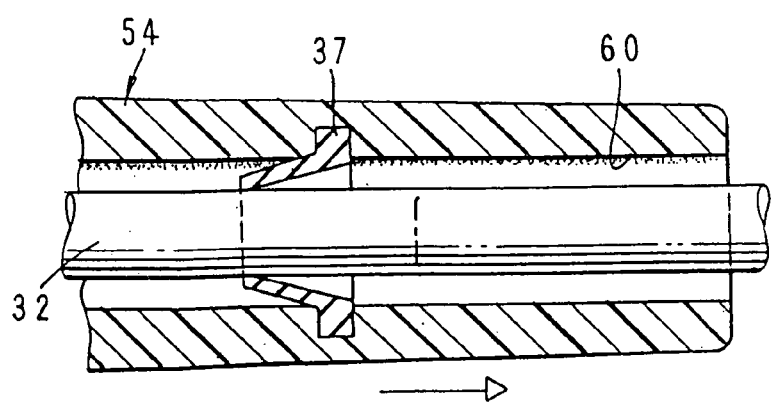
FIG. 22 is a greatly enlarged cross sectional view of the area designated in FIG. 16 by the numeral 22.

As is best seen by also referring to FIGS. 4, 5 and 6, in the present form of the invention, catheter 34 is provided with a first passageway 36 through which the guidewire 32 can be slideably moved. As illustrated in FIG. 3, first passageway 36 is coaxially aligned with axial center line 34c. By way of example, first passageway 36 may have a diameter of about 00.035 inches, has a proximal end 36a and a distal end 36b. As will presently be discussed in greater detail, an important feature of the apparatus of the present invention is a novel valve means that is disposed proximate distal end 36b of first passageway 36 for opening and closing the first passageway. Uniquely, this important valve means is movable by the guide wire 32 from a closed position shown in FIGS. 10, 11 and 13 to an open position shown in FIG. 12. When the valve means is in the closed position illustrated in FIGS. 10 and 13, the flow of loose debris such as embolic material through the first passageway 36 toward the proximal end of the catheter is substantially blocked. In the present form of the invention, this important valve means comprises a check valve 37 that is here provided as a partition 37a that spans the central passageway in the manner shown in FIG. 10. Uniquely partition 37a has a yieldably deformable central portion that is provided with a pair of crossing, perpendicularly extending slits 37b (FIG. 11). With this construction, when the guide wire impinges upon the check valve, it will force the slits 37b into the open configuration shown in FIG. 12 permitting free passage of the guide wire past the valve means. When the guide wire is retracted, in the manner shown in FIG. 13, the slitted portion of the valve will return to the starting, closed configuration shown in FIGS. 10 and 11. Partition 37a can be constructed of any suitable, semi-rigid plastic material.

Catheter 34 is also provided with a second side passageway or lumen 38 that is spaced apart from first passageway 36. As best seen in FIG. 3, second passageway 38 has an inlet 38a and an outlet 38b. Additionally, catheter 34 is provided with a third passageway or lumen 40 that is also spaced apart from first passageway 36. As indicated in FIG. 3, third passageway 40 has an inlet 40*a* and an outlet 40*b*.

Mounted on cannula 34 proximate the distal end thereof is an angioplasty balloon 42. Balloon 42, which is of conventional construction, is inflatable through the second passageway 38 with which it is in communication. In a conventional manner, balloon 42 is inflatable at deployment to about the diameter of the body vessel within which the catheter is inserted.

Balloon 42 may be formed of a compliant or non-compliant material, such as polyethylene or other standard balloon materials. Suitable materials for the construction of balloon 42 include a copolymer polyolefin material available from E.I. DuPont de Nemours and Co. of Wilmington, Del. By way of example, balloon 42 may have a length of about 1 cm and a wall thickness of between about 0.0007 and about 0.004".

Mounted on cannula 34 intermediate the proximal and distal ends thereof is an expandable means for expanding a stent. This expandable means is here provided as a stent balloon 44. Stent balloon 44, which is also of conventional construction, is inflatable through the third passageway 40 with which it is in communication. Stent balloon 44 may be manufactured from a substantially flexible and resilient material, such as polyethylene, polyester, latex, silicone, or more preferably polyethylene and polyester. A variety of balloons for stenting procedures are commercially available and have a wide range of known inflated lengths and diameters, allowing an appropriate balloon to be chosen specifically for the particular vessel being treated. By way of example, stent balloon 44 of the apparatus of the present invention may be of a length of between approximately 8 and 30 mm.

As best seen in FIG. 3, a radially expandable stent 48 is mounted on and circumscribes stent balloon 44. Stent 48, which is of conventional construction and is readily commercially available from various sources, may comprise a tube, sheet, wire, mesh or spring. In the present form of the invention, stent 48 comprises a substantially cylindrical wire mesh sleeve that is substantially rigid, yet expandable when subjected to radial pressure. While various materials may be used in the construction of the stent, materials such as stainless steel or nitinol, are preferable with stainless steel being most preferred.

As will be discussed in greater detail in the paragraphs which follow, in accordance with procedures well known to those skilled in the art, once the stent 48 is in the proper position, a fluid is introduced through the inflation lumen 40 to inflate the balloon 44. As the balloon 44 expands, the fluid pressure exerted on the stent forces the stent radially outwardly to engage plaque formed on the vessel wall. The expanding stent functions to push the plaque away from the region and to open the vessel. The stent 48, which generally covers a substantial portion of the plaque, traps it between the stent and the wall of the vessel. Once the stent is in place, balloon 44 is deflated by withdrawing the fluid out of the inflation lumen 40 and the catheter 34 is withdrawn from the patient using conventional methods. The stent 48 remains in place, substantially permanently covering the plaque in the treated region and forming part of the lumen of the vessel. For a purpose presently to be described, an aperture 49 is provided in the cannula wall at a location between the stent balloon 44 and the angioplasty balloon 42 (see FIG. 3).

As the stenosed region is being opened, by the balloon stent and the stent 48, plaque may break loose from the wall of the vessel. The various forms of the method of the present invention are specifically directed to taking steps to prevent this type of debris from traveling downstream of the vessel of the patient.

One form of the method of the invention, which is carried out using the apparatus of the invention shown in FIGS. 1 through 13, comprises the steps of first advancing the guide wire and then the catheter through a vessel of the patient in a conventional manner until the radially expandable stent is disposed proximate the stenosis. This done, fluid is introduced into the inlet of the second passageway to inflate the angioplasty balloon to a position in engagement with the wall of the vessel of the patient to block the downstream passage of emboli past the inflated angioplasty balloon. With the angioplasty balloon in inflated condition, the guide wire is withdrawn from the first passageway of the catheter to move the valve means of the invention into a closed positioned to thereby substantially block blood and loose debris flow through the first passageway of the catheter in a direction toward the proximal end thereof. Next, a fluid is introduced into the inlet of the third passageway to inflate the stent balloon to a position wherein the stent is at least partially imbedded into the wall of the dilated stenosis. With the stent thus properly positioned, the stent balloon is deflated. Next, using the aspirating pump 51, the fluid and embolic material that is within the artery of the patient is aspirated from the artery via aperture 49 (see FIG. 1). Following the aspirating step, the angioplasty balloon is deflated and the catheter, the stent balloon, the angioplasty balloon and the guide wire are removed from the vessel of the patient.

Referring next to FIGS. 14 through 22, an alternate, form of the invention is there shown and generally designated by the numeral 50. This alternate system is similar in many respects to that shown in FIGS. 1 through 13 and like numerals are used in FIGS. 14 through 22 to identify like components. Turning particularly to FIGS. 14, 15 and 16, this alternate form of the invention can be seen to comprise comprises a guide wire 32 and an elongated catheter 54 having a proximal end 54*a*, a distal end 54*b* and an axial center line 54*c*. As before, catheter 54 is preferably formed of a biocompatible and hydrophilic compatible material, such as a lubricous polyimide or polyethylene.

As best seen in FIG. 16, catheter 54 is provided with a first centrally disposed passageway 56 and a pair of side passageways 58 and 60. Passageway 58 is provided with an inlet port 58*a* and an outlet port 58*b*. Guide wire passageway 60, which is also provided with an inlet port 60*a* and an outlet port 60*b*, slidably receives the guide wire 32. For a purpose presently to be described, passageway 56 is in communication with the vessel of the patient via an aperture 62 provided in a sidewall of the catheter.

As in the early air described embodiment of the invention, novel valve means, which valve means are identical to that previously described herein, are disposed proximate the distal end 60*b* of passageway 60 for opening and closing the passageway. Like the earlier described valve means, this latter valve means is movable by guide wire 32 from a closed position to an open position shown in FIG. 22. When the valve means is in the closed position, the flow of blood and embolic material through passageway 60 toward the proximal end 60*a* thereof is substantially blocked.

Mounted on cannula 54 proximate the distal end thereof is an angioplasty balloon 42. Balloon 42, which is of the conventional construction previously described, is inflatable through guide wire passageway 60 with which it is in communication (see FIG. 16). In a conventional manner, balloon 42 is inflatable at deployment to about the diameter of the body vessel in which the catheter is inserted.

Mounted on cannula 54 intermediate the proximal and distal ends thereof is a stent balloon 44. By way of example, stent balloon 44 is spaced from balloon 42 by a distance of approximately 10 cm. stent balloon 44, which is of conventional construction previously described, is inflatable through side passageway 58 with which it is in communication. As before, stent balloon 44 may be manufactured from a substantially flexible and resilient material, such as polyethylene, polyester, latex, silicone, or more preferably polyethylene and polyester.

As best seen in FIG. 16, a radially expandable stent 48 of the character previously described is mounted on and circumscribes stent balloon 44. As in the earlier described embodiment, stent 44 is substantially rigid, yet expandable when subjected to radial pressure. Once the stent 48 is in the proper position, a fluid is introduced through the side inflation lumen 58 to inflate the balloon 44. As the balloon 44 expands, the fluid pressure exerted on the stent forces the stent radially outwardly to engage plaque formed on the vessel wall. The expanding stent functions to push the plaque away from the region and to open the vessel. The stent 48, which substantially covers the plaque, positions it between the stent and the wall of the vessel. Once the stent is in place, balloon 44 is deflated by withdrawing the fluid out of the inflation lumen 58 with the angioplasty balloon still inflated, blood and loose debris is aspirated from the vessel in a conventional manner via aperture 62. Withdrawal of the guide wire causes the valve means or check valve 37 to close, thereby substantially blocking the flow of loose debris into passageway 60 of the catheter. Following the aspiration step, the catheter if removed from the patient using conventional methods. The stent 48, of course, remains in place, substantially permanently covering the plaque in the treated region and forming part of the lumen of the vessel.

An alternate form of the method of the invention is carried out using the apparatus shown in FIGS. 14 through 22. This alternate method of the invention comprises the steps of first advancing the guide wire and the catheter through a vessel of the patient until the radially expandable stent is disposed proximate the stenosis. This done, a fluid is introduced into the inlet of the guide wire passageway passageway to inflate the angioplasty balloon to a position in engagement with the wall of the vessel. With the angioplasty balloon thus inflated, downstream passage of emboli is substantially blocked. Next, the guide wire is withdrawn from the guide wire passageway of the catheter to move the valve means into a closed positioned to substantially block the flow of loose debris through the guide wire passageway of the catheter in a direction toward the proximal end thereof. With the valve means closed, a fluid is next introduced into the inlet of the side passageway to inflate the stent balloon until the stent is properly imbedded into the wall of the dilated stenosis. Following the deflation of the stent balloon, the fluid and embolic material trapped within the artery of the patient is aspirated therefrom via the opening provided in the wall of the catheter. When the aspiration step is completed, the angioplasty balloon can be deflated and the catheter along with the stent balloon, the angioplasty balloon and guide wire can be removed from the vessel of the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A catheter system for balloon angioplasty and the delivery out a stent within the vessel of a patient comprising:
    (a) a catheter having a proximal end and distal end, said catheter having a wall provided with an aperture in communication with the vessel of the patient, said catheter including:
        (i) a first passageway having a proximal end and a distal end;
        (ii) a second passageway spaced-apart from said first passageway, said second passageway having an inlet and an outlet;
        (iii) a third passageway spaced-apart from said first passageway, said third passageway having an inlet and an outlet;
    (b) a guide wire movable within said first passageway;
    (c) valve means disposed within said first passageway within which said guide wire is movable for opening and closing said passageway, said valve means being moved from a closed position to an open position by movement of said guide wire;
    (d) a radially expandable stent mounted on said cannula proximate said outlet of one of said first, second and third passageways;
    (e) an angioplasty balloon mounted on said cannula proximate said distal end thereof, said angioplasty balloon being in communication with said outlet of one of said first, second and third passageways; and
    (f) an aspirating pump in communication with said first passageway for aspirating material from the vessel of the patient via the aperture provided in the catheter wall.

2. The catheter system as defined in claim 1 in which said valve means comprises a partition having a yieldably deformable central portion.

3. The catheter system as defined in claim 1, further including expandable means mounted on said catheter for radially expanding said stent.

4. The catheter system as defined in claim 1 in which is selected one of said first, second and third passageways is in communication with the vessel of the patient via an opening formed in the wall of said cannula.

5. A catheter system for balloon angioplasty and stent delivery comprising:
    (a) a guide wire;
    (b) a catheter having a proximal end, a distal end and a wall having an aperture therein, said catheter including:
        (i) a first passageway through which the guide wire can be slideably moved, said first passageway having a proximal end and a distal end;
        (ii) valve means disposed proximate said distal end of said first passageway for opening and closing said first passageway, said valve means being moved from a closed position to an open position by said guide wire;
        (iii) a second passageway spaced-apart from said first passageway, said second passageway having an inlet and an outlet;
        (iv) a third passageway spaced-apart from said first passageway, said third passageway having an inlet and an outlet;

(c) a radially expandable stent mounted on said cannula proximate said outlet of said third passageway;

(d) an angioplasty balloon mounted on said cannula proximate said distal end thereof, said angioplasty balloon being in communication with said outlet of said second passageway; and (e) an aspirating pump in communication with said first passageway for aspirating material from the vessel of the patient via the aperture in said wall of said wall.

6. The catheter system as defined in claim 5 in which said valve means comprises a partition having a yieldably deformable central portion.

7. The catheter system as defined in claim 5 in which said catheter has an axial centerline and in which said first passageway is aligned with said axial centerline.

8. The catheter system as defined in claim 5, further including expandable means mounted on said catheter for radially expanding said stent.

9. A catheter system for balloon angioplasty and stent delivery comprising:

(a) an elongated, flexible guide wire;

(b) an elongated, flexible catheter having a proximal end, a distal end and a wall having an aperture therethrough, said flexible catheter including:

(i) a first central passageway through which the guide wire can be slideably moved, said first central passageway having a proximal end and a distal end;

(ii) valve means disposed proximate said distal end of said first passageway for opening and closing said first passageway, said valve means comprising a check valve movable from a closed position to an open position by said guide wire;

(iii) a second passageway spaced-apart from said first passageway, said second passageway having an inlet and an outlet;

(iv) a third passageway spaced-apart from said second passageway, said third passageway having an inlet and an outlet;

(c) a radially expandable stent mounted on said cannula proximate said outlet of said third passageway;

(d) expandable means mounted on said catheter for radially expanding said stent;

(e) an angioplasty balloon mounted on said cannula proximate said distal end thereof, said angioplasty balloon being in communication with said outlet of said second passageway; and (f) an aspirating pump in communication with said first passageway for aspirating material from the vessel of the patient via the aperture in said wall of said catheter.

10. The catheter system as defined in claim 9 in which said check valve comprises a partition spanning said central passageway, said passageway having a central portion and a pair of crossing, perpendicularly extending slits formed in said central portion.

11. The catheter system as defined in claim 9 in which said expandable means for radially expanding said stent comprises a stent balloon mounted on said catheter for communication with said outlet of said third passageway.

12. The catheter system as defined in claim 11 further including means for introducing a fluid into said inlet of said second passageway.

13. The catheter system as defined in claim 12 further including means for introducing a fluid into said inlet of said third passageway.

14. A method for placing a stent within a stenosis in a vessel of a patient using a catheter system comprising a catheter having a wall provided with an aperture therethrough, the catheter system further comprising an aspirating pump; a guide wire; a catheter having a proximal end and distal end and including a first passageway through which the guide wire can be slideably moved, said first passageway having a proximal end and a distal end; valve means disposed proximate said distal end of said first passageway for opening and closing said first passageway, said valve means being moved from a closed position to an open position by said guide wire; a second passageway spaced-apart from said first passageway, said second passageway having an inlet and an outlet; a third passageway spaced-apart from said first passageway, said third passageway having an inlet and an outlet; an angioplasty balloon mounted on said cannula proximate said distal end thereof, said angioplasty balloon being in communication with said outlet of said second passageway; and a stent balloon and a radially expandable stent mounted on said cannula proximate said outlet of said third passageway; said method comprising the steps of:

(a) advancing the guide wire and the catheter through a vessel of the patient until the radially expandable stent is disposed proximate the stenosis;

(b) introducing a fluid into the inlet of the second passageway to inflate the angioplasty balloon to a position in engagement with the wall of the vessel of the patient to block the passage of emboli past the inflated angioplasty balloon;

(c) withdrawing the guide wire from the first passageway of the catheter to move the valve means into a closed position to substantially block the flow of loose debris through the first passageway of the catheter in a direction toward the proximal end thereof;

(d) introducing a fluid into the inlet of the third passageway to inflate the stent balloon until the stent is properly imbedded into the wall of the dilated stenosis;

(e) deflating the stent balloon;

(f) aspirating loose materials from the vessel of the patient;

(g) deflating the angioplasty balloon; and (h) removing the catheter along with the stent balloon, the angioplasty balloon and guide wire from the vessel of the patient.

15. A method for placing a stent within a stenosis in a vessel of a patient using a catheter system comprising a catheter having a sidewall having an aperture therethrough, said catheter system further comprising an aspirating pump, a guide wire; a catheter having a proximal end and distal end and including a guide wire passageway through which the guide wire can be slideably moved; said passageway having a proximal end and a distal end; valve means disposed proximate said distal end of said passageway for opening and closing said passageway, said valve means being moved from a closed position to an open position by said guide wire; a central passageway spaced-apart from said guide wire passageway, said central passageway having an inlet and an outlet and being in communication with the artery of the patient via said aperture in said sidewall of the catheter; a side passageway spaced-apart from said central passageway, said side passageway having an inlet and an outlet; an angioplasty balloon mounted on said cannula proximate said distal end thereof, said angioplasty balloon being in communication with said outlet of said guide wire passageway; and a stent balloon and a radially expandable stent mounted on said cannula proximate said outlet of said side passageway; said method comprising the steps of:

(a) advancing the guide wire and the catheter through a vessel of the patient until the radially expandable stent is disposed proximate the stenosis;

(b) introducing a fluid into the inlet of the guide wire passageway to inflate the angioplasty balloon to a position in engagement with the wall of the vessel of the patient to block the downstream passage of emboli past the inflated angioplasty balloon;

(c) withdrawing the guide wire from the guide wire passageway of the catheter to move the valve means into a closed position to substantially block the flow of loose debris through the guide wire passageway of the catheter in a direction toward the proximal end thereof;

(d) introducing a fluid into the inlet of the side passageway to inflate the stent balloon until the stent is properly imbedded into the wall of the dilated stenosis;

(e) deflating the stent balloon;

(f) using said aspirating pump, aspirating fluid and embolic material from the artery of the patient via the opening provided in the wall of the catheter;

(g) deflating the angioplasty balloon; and (h) removing the catheter along with the stent balloon, the angioplasty balloon and guide wire from the vessel of the patient.

* * * * *